(12) United States Patent
Conner

(10) Patent No.: US 11,224,256 B2
(45) Date of Patent: Jan. 18, 2022

(54) PD-UWEAR: PERITONEAL DIALYSIS UNDERGARMENTS

(71) Applicant: Mary Conner, Stockbridge, GA (US)

(72) Inventor: Mary Conner, Stockbridge, GA (US)

(*) Notice: Subject to any disclaimer, the term of this patent is extended or adjusted under 35 U.S.C. 154(b) by 274 days.

(21) Appl. No.: 16/009,604

(22) Filed: Jun. 15, 2018

(65) Prior Publication Data
US 2019/0133200 A1 May 9, 2019

Related U.S. Application Data

(60) Provisional application No. 62/581,726, filed on Nov. 5, 2017.

(51) Int. Cl.
| | | |
|---|---|---|
| *A41B 9/12* | (2006.01) | |
| *A41B 9/00* | (2006.01) | |
| *A41D 27/20* | (2006.01) | |
| *A61M 1/28* | (2006.01) | |

(52) U.S. Cl.
CPC ............. *A41B 9/12* (2013.01); *A41B 9/001* (2013.01); *A41D 27/201* (2013.01); *A41B 2300/32* (2013.01); *A41B 2400/32* (2013.01); *A41D 2300/32* (2013.01); *A61M 1/285* (2013.01); *A61M 2209/088* (2013.01)

(58) Field of Classification Search
CPC ....... A61M 2025/0206; A61B 2400/32; A61B 9/12
See application file for complete search history.

(56) References Cited

U.S. PATENT DOCUMENTS

| | | | | |
|---|---|---|---|---|
| 5,496,282 A | * | 3/1996 | Militzer | A61M 25/02 604/179 |
| 6,041,445 A | * | 3/2000 | Davitt | A41B 9/007 2/247 |
| 6,126,639 A | | 10/2000 | Sutherland | |
| 6,202,222 B1 | | 3/2001 | Robbins | |
| 2018/0177242 A1 | * | 6/2018 | Johnson | A41B 9/007 |

OTHER PUBLICATIONS

CN207462375, Jun. 2018, Wang (Year: 2018).*
CN207679782, Aug. 2018, He (Year: 2018).*

* cited by examiner

*Primary Examiner* — Sarah B McPartlin
(74) *Attorney, Agent, or Firm* — Ronald D. Baker

(57) ABSTRACT

The present invention is a peritoneal undergarment for alleviating unpleasant irritation while receiving dialysis treatment. The current method of taping the transfer set is not effective during dialysis treatment due to the constant irritation while the patient's skin is pressed against the dialysis port. The present invention is a specially designed peritoneal undergarment that is effective at relieving pain while dialyzing. The current invention is ideal to combat irritation and can be manufactured using a variety of materials such as cotton which may be washed with household detergent.

17 Claims, 5 Drawing Sheets

PD-UWEAR: PERITONEAL DIALYSIS UNDERGARMENTS

The present application claims priority to the earlier fled provisional application having Ser. No. 62/581,726, and hereby incorporates subject matter of the provisional application in its entirety.

TRADEMARK NOTICE

Trademarks are the property of their respective owners.

FIELD OF INVENTION

The subject disclosure relates to a Peritoneal Undergarment for alleviating irritation and distress while dialyzing. More particularly, the present disclosure relates to a novel undergarment that provides an ideal experience for users who have to periodically receive such treatments.

BACKGROUND

Conventional peritoneal undergarments are considered items of underwear worn by a user for purposes of receiving critical dialysis treatment. Traditionally, this experience can be painful and often irritating due to the various types of equipment that may come in contact with a person's skin during treatment or during normal wear. Peritoneal undergarments prior to PD-Uwear, have been inconvenient and an uncomfortable ordeal for those who have to live with such treatments. Not only do users have to move around from day-to-day with the undergarments but often they have to sleep with such undergarments which can be excruciating due to the attachments that accompany dialysis treatment.

Users have dealt with traditional peritoneal undergarments but are eager to embrace a novel option to the conventional brand of such undergarments in the marketplace. Although the use of peritoneal undergarments is necessary for those who have to live with dialysis treatments but it does not have to be a painful or inconvenient experience for a user. PD-Uwear is comfortable because users do not have to resort to using tape to hold the transfer tubing in place, they are sanitary because they can be washed in regular laundry, they are convenient due to their unique construction, and lastly, they are safe as a result of how the garment holds the transfer set in place without dangling.

BRIEF SUMMARY

The proposed invention is a peritoneal undergarment as outlined which allows users to benefit from a broader range of comfort while dialyzing which protects the user from the pain and irritation associated with wearing bulky equipment while sleep or carrying on daily activities. The present invention is configured using specially placed pockets and guides to provide comfort and prevents the user from suffering skin irritation from external devices associated with a transfer set is the focus of the present embodiment. The user has the option to purchase a garment that has a single pocket on the outer surface or pockets that are symmetrically placed for the purpose of concealing the transfer tubing in the open end of the pocket that is located along the inner surface. The current method of receiving dialysis treatment for many who have to wear such undergarments day and night can be an excruciating ordeal in those are that do not have adequate coverage to protect from such irritation. To further elaborate, the current embodiment maximizes coverage for the transfer set that provides comfort at points that would otherwise increase the level of irritation that a user would experience. The present undergarment can be worn as ordinary underwear that can be washed with regular laundry detergent. PD-Uwear is an invention that will offer users a safe, comfortable, convenient, and sanitary solution to the conventional method of wearing peritoneal underwear while receiving dialysis treatment.

Balancing the need for undergarments that provide versatility with the need to be able to carry on daily activities has led to changes in peritoneal design. For example, U.S. Pat. No. 6,202,222 to Robbins sets forth a garment having a front, back, crotch panels, waist, leg bands for accommodating an ostomy appliance that is worn by patients having undergone an ileostomy, colostomy, or the like. However, the Robbins garment is intended for merely securing an ostomy appliance, the prior invention does not address the comfort, safety, and convenience the current invention addresses. In this application for dialysis patients but rather the prior art in the Robbins disclosure focuses on primarily a method of concealing an ostomy appliance within a pouch.

U.S. Pat. No. 6,126,639 to Sutherland et al. describes a peritoneal dialysis catheter support undergarment which includes an undergarment that can be worn under clothing to hold a catheter tube within a pocket. The construction discloses durable straps to hold the undergarment around the user and allows for a secure fit in order to hold the catheter tube in place against the user's body while not dialyzing. However, this embodiment does not solve the problem of providing increased comfort for the user since as presented will expose the user's skin to a greater area of irritation thus resulting in infections since the portion of the tube that is not inserted into the pocket is free to move and cause skin irritation for the user due to constant skin contact.

The subject matter of each of the above U.S. patents is herein incorporated by reference.

It is an object of the present invention to overcome the deficiencies of the prior art by providing an undergarment which is manufactured to carefully select soft material for convenience and to eliminate skin irritation that can cause distress among users.

Therefore, there exists a need in the art for an undergarment which protects a greater portion of a user's skin while at the same time securing the transfer tubing in a way that will not allow the tubing to freely move or dangle in a manner to increase the risk of sanitation concerns, particularly a portion of a user's abdomen and groin area while in movement.

BRIEF DESCRIPTION OF THE DRAWINGS

Certain illustrative embodiments illustrating objects and advantages may be best understood by reference detailed description that follows taken in conjunction with the accompanying drawings in which.

DETAILED DESCRIPTION

Figure 1:
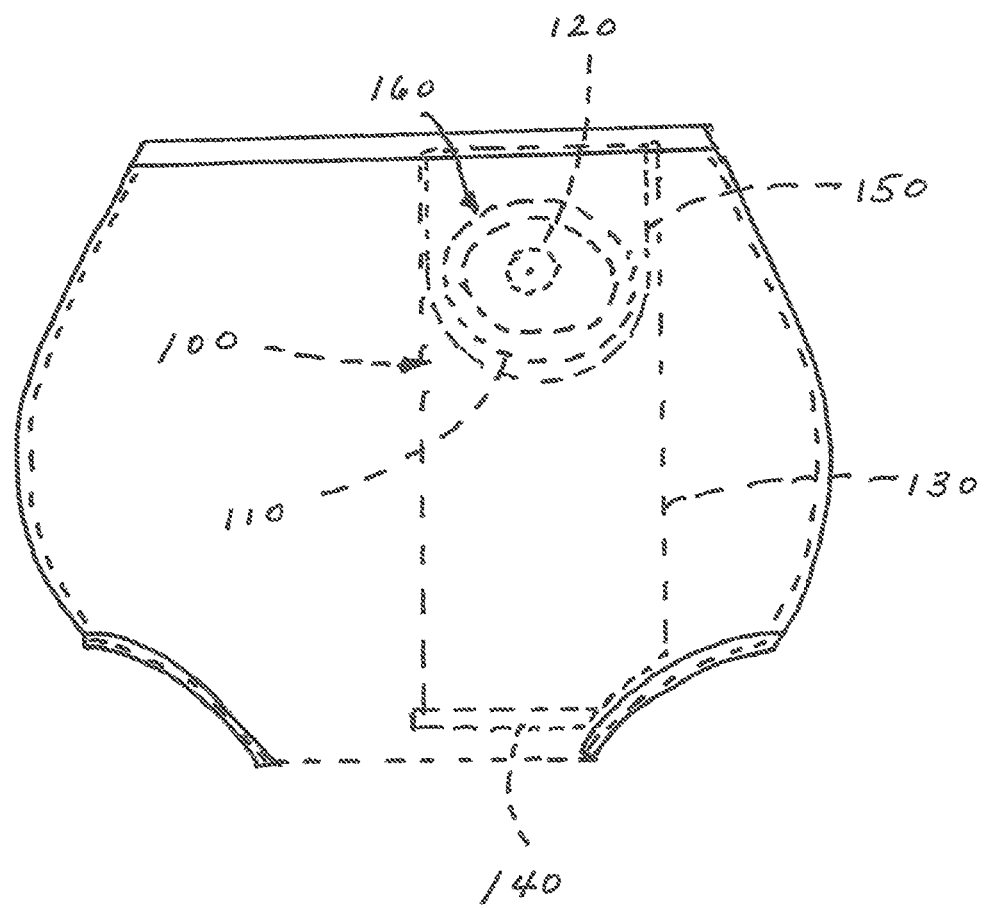
FIG. 1 is a schematic drawing of an ostomy appliance/garment according to the invention.

While this invention is susceptible of embodiment in many different forms, there is shown in the drawings and will herein be described in detail specific embodiments, with the understanding that the present disclosure of such embodiments is to be considered as an example of the principles and not intended to limit the invention to the specific embodiments shown and described. In the description below, like reference numerals are used to describe the same, similar or corresponding parts in the several views of the drawings.

The terms "a" or "an", as used herein, are defined as one, or more than one. The term "plurality", as used herein, is defined as two, or more than two. The term "another", as used herein, is defined as at least a second or more. The terms "including" and/or "having", as used herein, are defined as comprising (i.e., open language). The term "coupled", as used herein, is defined as connected, although not necessarily directly, and not necessarily mechanically.

Reference throughout this document to "one embodiment", "certain embodiments", "an exemplary embodiment" or similar terms means that a particular feature, structure, or characteristic described in connection with the embodiment is included in at least one embodiment of the present invention. Thus, the appearances of such phrases or in various places throughout this specification are not necessarily all referring to the same embodiment. Furthermore, the particular features, structures, or characteristics may be combined in any suitable manner in one or more embodiments without limitation.

Reference throughout this document to "pocket" or similar terms refers to a small hollow compartment that allows the transfer tube to be inserted for purposes of holding the transfer set in order to protect a user's skin from the surface of an external instrument by insulating the transfer tube. Thus, the appearance of similar phrases throughout this specification may not be limited to just the term "pocket" but when the description refers to a means of securing the transfer set then it may be inferred that the description refers to a pocket.

Reference throughout this document to terms such as "open end" or "space" refers to areas of the proposed invention where objects maybe inserted for storage or similar purposes. For instance, where a pocket is described that allows an object such as a transfer tube to be inserted would be an example of an open end of the pocket which would allow the transfer set to be stored in the space provided by the open end. Thus, the appearance of similar phrases throughout this specification may not be limited to just the term "open end" or "space" but when the description refers to a location or area where the transfer set is inserted or stored then it may be inferred that the description refers to an "open end" or "space".

Reference throughout this document to "panel" refers to the portions of the undergarment that make up the inner and outer wall of the undergarment. Furthermore, the particular features, structures, or characteristics may be combined in any suitable manner in one or more embodiments without limitations.

Reference throughout this document to tube guide refers to a structure for securing external devices to the peritoneal undergarments such as straps but Is not limited to this example. Therefore, where ever this specification refers to a tube guide it may refer to various material that may be combined to create a tube guide for purposes of the present embodiment.

The material a peritoneal undergarment is made of is an essential aspect to the garment because it determines the quality of the undergarment and often dictates a user's experience. From a comfort perspective, the type of material that the undergarment is made of affects the user's sensory factors and is an important attribute for effectively presenting a more inviting undergarment garment. In common use of peritoneal undergarments, manufacturers do not apply components to the undergarment for purposes of minimize stress and trauma associated with receiving dialysis treatments. In a non-limiting example, because comfort is important to wearing such undergarments then a combination of soft material, fabric liner made by special liners such as nylon, cotton, and spandex can be used to provide a pleasant experience for the user. Conventional peritoneal undergarments prior to PD-Uwear did little to provide comfort to patients but merely held the transfer set against a user's skin during the treatments; this does little to alleviate the pain and trauma that users experience while receiving dialysis treatments. Using a combination of various soft materials, linens, a fabric liner, and strategic positioning of various attachments provides an effective method of helping to eliminate irritation and ensuring a pleasant experience while wearing the present invention. In a non-limiting example, the pocket and tube guide of the undergarment can be made of an ultra-soft material that provides an extra comfortable barrier between the transfer tubing and the user's skin.

In the exemplary embodiment, the current invention consists of an undergarment made from a comfortable cloth material which has an outer pocket attached to the front panel of the outer fabric lining of the undergarment at a location that comfortably allows the transfer set to be inserted near a patient's catheter. In an alternate embodiment, the undergarment can be manufactured with an optional symmetric inner pocket which is attached to the inner surface of the front panel. The undergarment helps to ensure a secure fit to eliminate irritation experienced due to the transfer set and additionally minimizing movement that is often associated with dialysis treatments. The peritoneal undergarment allows the user to sleep comfortably and also perform daily tasks without irritation associated to bulky or dangling transfer tubing.

In an additional embodiment the tube guide may Include a variety of different configurations, by a non-limiting example, hook and loop fasteners such as Velcro® attachments can be used for the tube guide allowing the patient to attach the transfer set to the inner surface of the peritoneal undergarment without the difficulty of removing the undergarment. The user can simply use a convenient hook and loop fastening flap which serves as the moveable portion of the tube guide.

In an alternate embodiment. PD-Uwear may be used for all types of medical and non-medical purposes for humans and animals alike that require comfort due to external devices. The undergarment can be configured to address concerns by patients who in a non-limiting example may be forced to have a tube or other medical devices inserted in their abdomen area for various treatments or other purposes deemed fit for such use.

Turning now to FIG. 1, this is a schematic front view of an undergarment with a ostomy appliance attached. The ostomy appliance 100 is comprised of a wafer 110 having a circular disk or flange 120 which attaches to the stoma on the user's body. The ostomy flange 120 comes in different sizes and circumferences. The ostomy appliance 100 also has as part of its structure a pouch 130 for the collection of body wastes exiting the body through the stoma. The schematic illustrates an opening at the bottom through which body wastes can be emptied by a removable pouch clip closure 140. Additionally, the garment includes a hidden pocket 160 which includes a bound pocket opening 150.

Prior to PD-Uwear, such garments were designed to accommodate the user while receiving dialysis treatment with little thought to convenience and comfort which provided decreased confidence for the user. Prior designs included just simply using large pouches and other similar spaces. The problem with such broad stance is there is no real focus placed on increasing convenience for the user in a way to minimize discomfort created by bulky, lose and dangling tubing. In FIG. 1, the oversized pouch 130 as well as the pocket 160 allows for bulky storage which can result in skin irritation and inconvenience. PD-Uwear solves this problem experienced by users of the prior art.

The present embodiment has features that greatly minimizes discomfort and adds convenience for the user in way that the prior art of FIG. 1 did not apply.

Figure 2:
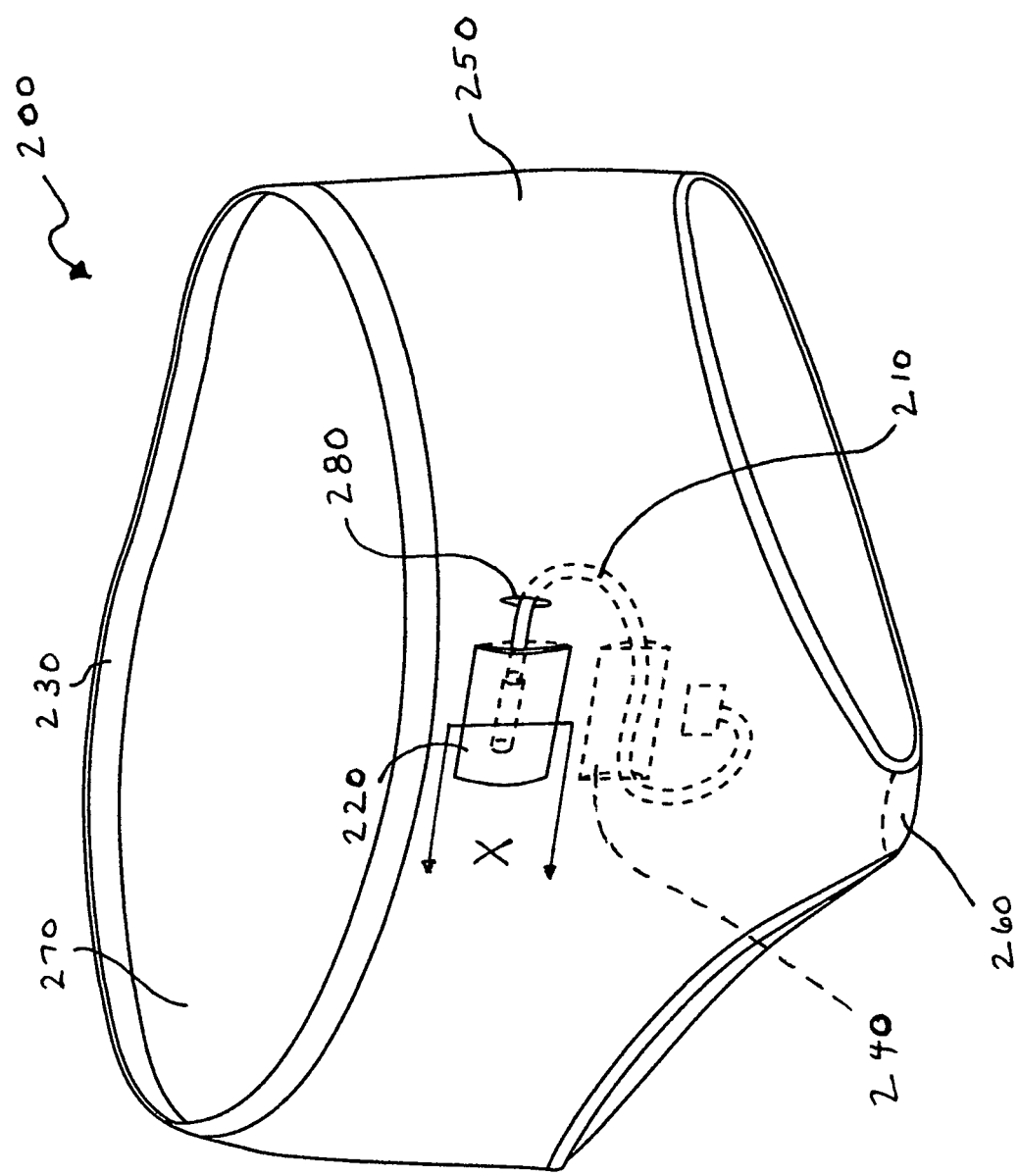
FIG. 2 is a diagram of a front-view of the proposed invention consistent with certain embodiments of the present invention.

Turning now to FIG. 2, this figure presents a view of the front-panel 250 of the peritoneal undergarment for an exemplary diagram of the garment 200 consistent with certain embodiments of the present invention. A peritoneal undergarment 200, that may be worn by the patient who must use a transfer set 210 during dialysis treatments. The pocket article 220 which secures the transfer set to the peritoneal undergarment 200. The peritoneal undergarment 200 includes a crotch section 260 and an elastic-waste band 230 along the top portion of the front and back panels of the garment to provide a comfortable fit. When the peritoneal undergarment 200 is securely fitted, the pocket 220 serves as a support for holding the transfer set 210 in place while not in use. The inner fabric lining 270 of the undergarment serves as an extra support layer that holds the transfer set in position. The material that make up the tube guide 240 is critical because it allows the user to experience comfort, convenience, and safety while receiving dialysis treatment. The tube guide prevents the tubing from moving in a way to prevent irritation due to skin contact. The combination of the inner surface of the undergarment, the ultra-soft material associated to the inner tube guide 240 of the undergarment, and the strategic location of the pocket and button hole 280 provides a pleasant barrier between the transfer set and the users body.

Figure 3:
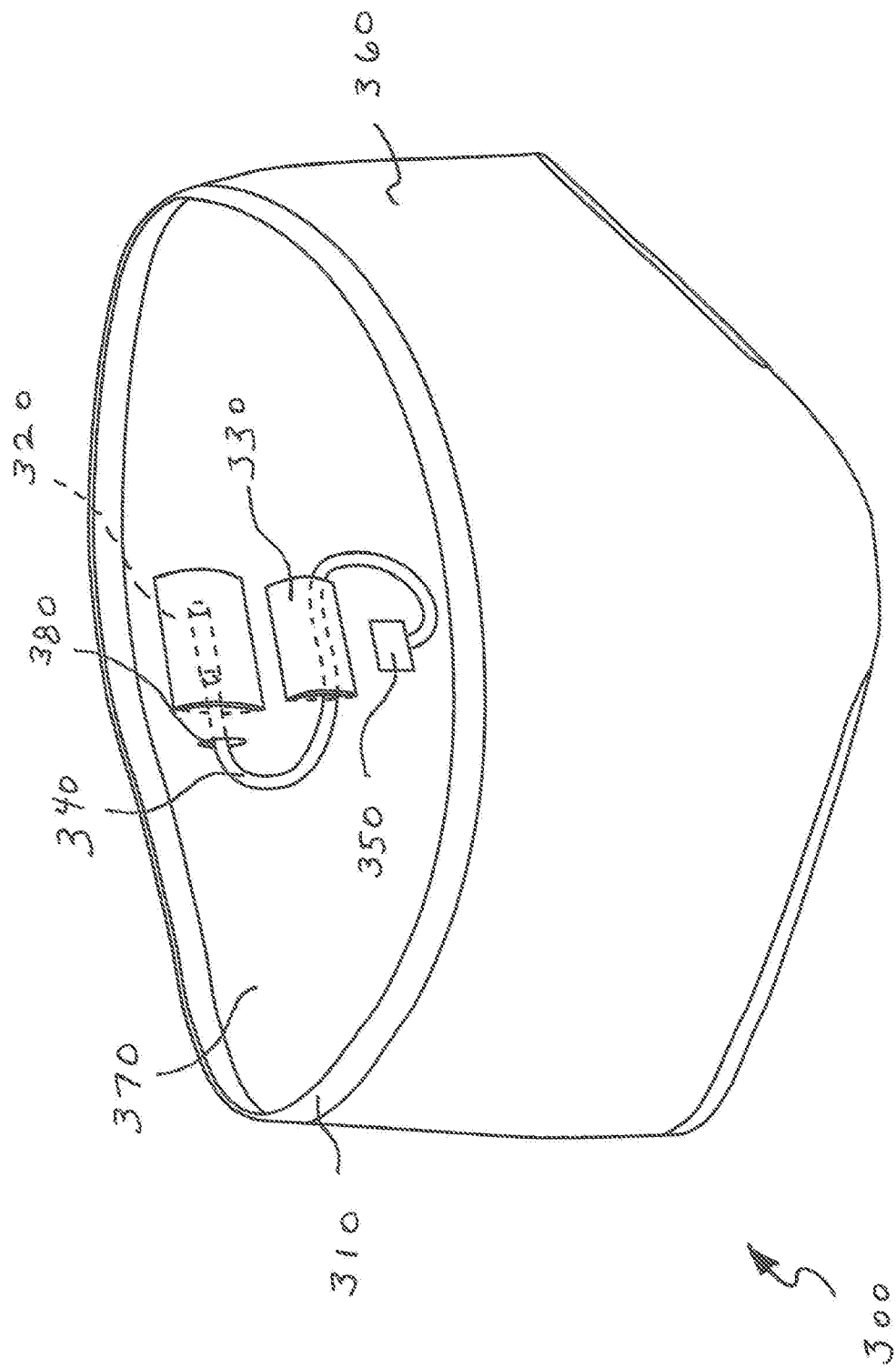
FIG. 3 is a diagram of a rear-view of the proposed invention which illustrates alternative attachments consistent with certain embodiments of the present invention.

Turning now to FIG. 3, this figure presents a rear view of the peritoneal undergarment for an exemplary diagram of the undergarment 300 consistent with certain embodiments of the present invention. The schematic illustrates a view of the back panel 360 of the undergarment 300, that depicts the transfer tubing 340 for the dialysis transfer set extending from the exit port 350 of a person's body which then extends through the tube guide 330 and then exits through a button hole 380 of the undergarment and extends inside the outer pocket 320. The outer pocket 320 serves as a safe storage while a user is not receiving dialysis treatments; the outer pocket 320 prevents the tubing from dangling in a manner that prevents injury or damage to the tubing and or user. The peritoneal undergarment 300 includes an elastic-waste band 310 and a fabric lining 370 along the top portion of both the front and back panels of the garment. The tube guide 330 secures the transfer set 340 which serves to alleviate irritation associated with contact made by the transfer set 340 against the user's body. The peritoneal undergarment 300 includes at least two pockets 320 which are strategically positioned to provide a pleasant experience.

Figure 4:
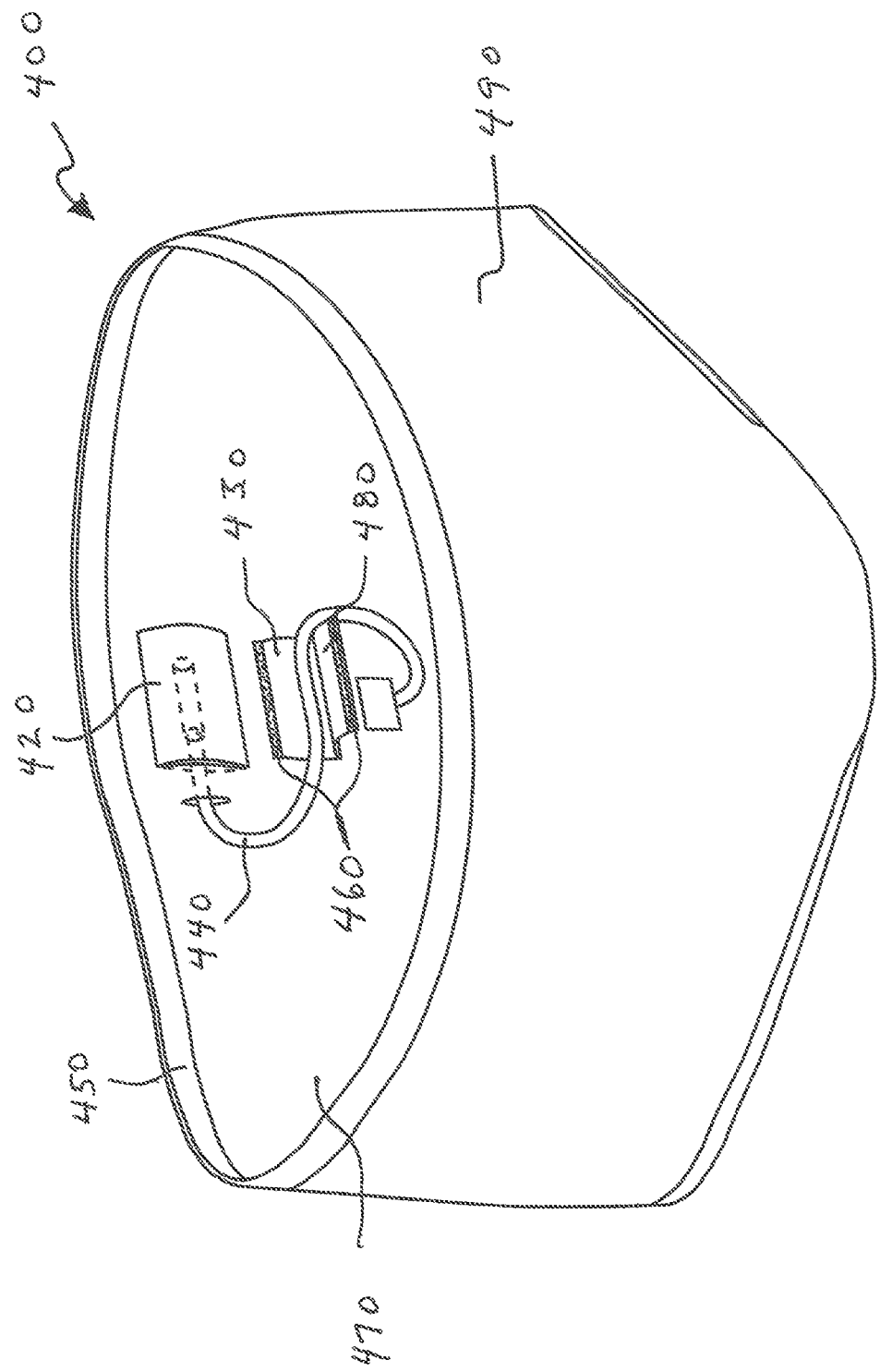
FIG. 4 is a diagram of a rear view of the embodiment to depict the inner surface of the garment consistent with certain embodiments of the present invention.

Turning now to FIG. 4, this figure presents the back panel 490 view of the undergarment 400 in an effort to depict the alternate inner pocket 420 as well as the tube guide 430 for an exemplary diagram of the undergarment consistent with certain embodiments of the present invention. The undergarment 400 includes an elastic-waste band 450 along the top portion of the front and back panels of the garment to provide a comfortable fit. The schematic intends to illustrate how both the inner pocket 420 and the tube guide 430 is configured along the inner fabric lining 470 of the undergarment 400. The schematic further depicts an alternate option for a hook and loop fastener 460 to be attached to the tube guide 430 which serves as a quick release of the transfer set 440 from the tube guide 430 by using the flap 430 in the event the user desires to reposition or remove the transfer set 440.

Figure 5:
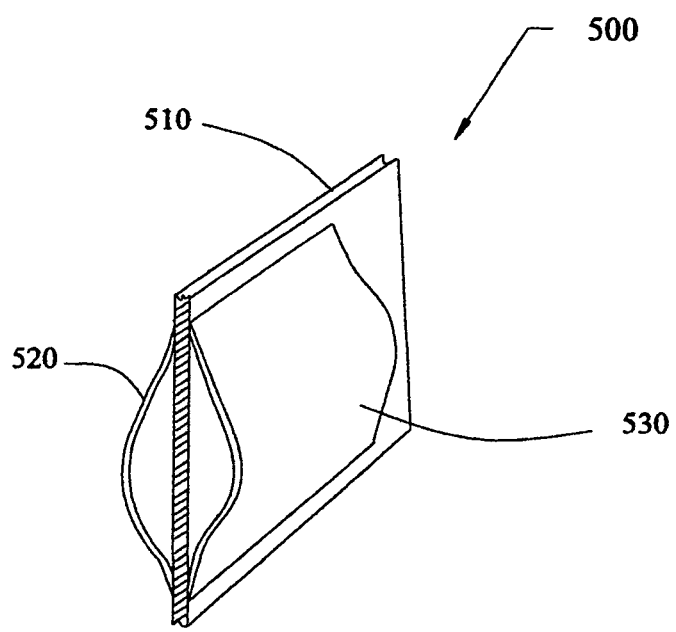
FIG. 5 is a cross-sectional view of the embodiment to depict the symmetrical pockets attached along both the inner surface and outer surface of the garment consistent with certain embodiments of the present invention.

Turning now to FIG. 5, this figure presents a cross-sectional view of the symmetrical pockets of the undergarment 500 in an effort to depict the inner pocket 530 as well as the outer pocket 520 conveniently located symmetrically opposite of each other in a mirror image fashion. The figure also depicts the liner 510 of the undergarment consistent with certain embodiments of the present invention. The schematic intends to illustrate how both the inner pocket 530 and the outer pocket 520 is configured along opposite sides of the panel 510 of the undergarment 500.

I claim:
1. A peritoneal undergarment comprising:
(a) a front panel surface; wherein the front panel surface is stitched to an elastic-waist band and a crotch panel;
(b) a back-panel surface; wherein the back panel surface is stitched to the front panel surface so as to form a structure for encircling a user's waist;
(c) the front and back panel surfaces both includes inner surfaces and a bottom portion opposite of the elastic-waist band;
(d) wherein the crotch panel is stitched to the bottom portion of both the front and back panel surfaces so as to form a crotch portion and so as to construct two leg openings for the undergarment;
(e) said elastic-waist band; wherein said elastic-waist band is stitched to said front and back panel surfaces;
(f) at least one pocket; wherein the pocket can be either attached to an inner fabric lining or outer surface of the undergarment in a symmetrical fashion positioned reflective of an opposite pocket;
(g) a button hole; wherein said button hole is located in a convenient location aligned to a opening of said pocket to accommodate an exit point for a catheter tube; and
(h) a tube guide; wherein said tube guide is attached to an inner fabric lining of the front panel.

2. The peritoneal undergarment according to claim 1, wherein the front panel further comprises the fabric lining joined to the inner surfaces of said front and back panels, wherein said fabric lining of front panel further includes said pocket and said tube guide.

3. The peritoneal undergarment according to claim 1, wherein the back panel surface further comprises the fabric lining joined to the inner surfaces of said front and said back panel.

4. The peritoneal undergarment according to claim 1, wherein said at least one pocket may further be comprised of soft cloth material.

5. The peritoneal undergarment according to claim 4, wherein said at least one pocket further comprises soft material that can be made to stretch.

6. The peritoneal undergarment according to claim 1, wherein said at least one pocket may be further joined to either the inner surfaces or an outer surface of the undergarment.

7. The peritoneal undergarment according to claim 6, wherein said at least one pocket located on either the fabric lining or outer surfaces are symmetric forming a mirror image of said at least one pocket.

8. The peritoneal undergarment according to claim 6, wherein the pocket further comprises an open end that allows objects to be inserted into the pocket.

9. The peritoneal undergarment according to claim 8, wherein the pocket further comprises three dosed sides with one dosed side positioned opposite of said open end of the a least one pocket.

10. The peritoneal undergarment according to claim 6, wherein the pocket joined to the fabric lining further comprises at least one hook and loop fastener attachment.

11. The peritoneal undergarment according to claim 10, wherein the hook and loop fastener is further positioned along at least one side portion of the pocket that meets the surface of the undergarment.

12. The peritoneal undergarment according to claim 1, wherein the undergarment contains the button hole that is large enough to allow the insertion of a catheter tube.

13. The peritoneal undergarment according to claim 1, wherein the tube guide is joined to the inner fabric lining of the front panel in a convenient manner to provide for satisfactory transition of a transfer tube as it exits the user's body as well as entering the pocket.

14. The peritoneal undergarment according to claim 13, wherein the tube guide further comprises an opening that is at least % inch in width and further includes at least one hook and loop fastener for ease of accessibility.

15. The peritoneal undergarment according to claim 13, wherein the tube guide is at least 2 inches in length.

16. The peritoneal undergarment according to claim 13, wherein the tube guide is attached to the in fabric lining of the undergarment in order to receive the transfer tube.

17. The peritoneal undergarment according to claim 1, wherein the tube guide is joined to the inner fabric lining at a horizontal position preferably to a left or a right side panel of the undergarment.

* * * * *